US00PP26922P2

(12) United States Plant Patent
Wood

(10) Patent No.: US PP26,922 P2
(45) Date of Patent: Jul. 12, 2016

(54) ***WEIGELA* PLANT NAMED 'SMNWFMS'**

(50) Latin Name: *Weigela florida*
Varietal Denomination: SMNWFMS

(71) Applicant: Timothy D. Wood, Spring Lake, MI (US)

(72) Inventor: Timothy D. Wood, Spring Lake, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 14/544,625

(22) Filed: Jan. 23, 2015

(51) Int. Cl.
*A01H 5/00* (2006.01)

(52) U.S. Cl.
USPC ..... Plt./226

(58) Field of Classification Search
USPC ..... Plt./226
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Weigela* plant named 'SMNWFMS', characterized by its compact and low-mounding plant habit; freely branching habit; dark burgundy to almost black-colored leaves; freely flowering habit; red purple-colored flowers; and good garden performance.

2 Drawing Sheets

Botanical designation: *Weigela florida*.
Cultivar denomination: 'SMNWFMS'.

BACKGROUND OF THE INVENTION

The present invention relates to a new and distinct cultivar of *Weigela* plant, botanically known as *Weigela florida* and hereinafter referred to by the name 'SMNWFMS'.

The new *Weigela* plant is a product of a planned breeding program conducted by the Inventor in Grand Haven, Mich. The objective of the breeding program was to develop new compact and low-mounding *Weigela* plants with attractive leaf and flower colors and cold hardiness.

The new *Weigela* plant originated from an open-pollination in May, 2009 of *Weigela florida* 'Verweig', disclosed in U.S. Plant Pat. No. 16,824, as the female, or seed, parent with an unknown selection of *Weigela florida*, as the male, or pollen, parent. The new *Weigela* plant was discovered and selected by the Inventor as a single flowering plant from within the progeny of the stated open-pollination in a controlled environment in Grand Haven, Mich. in June, 2011.

Asexual reproduction of the new *Weigela* plant by softwood cuttings since June, 2011 in Grand Haven, Mich. has shown that the unique features of this new *Weigela* plant are stable and reproduced true to type in successive generations of asexual reproduction.

SUMMARY OF THE INVENTION

Plants of the new *Weigela* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNWFMS'. These characteristics in combination distinguish 'SMNWFMS' as a new and distinct *Weigela* plant:

1. Compact and low-mounding plant habit.
2. Freely branching habit.
3. Dark burgundy to almost black-colored leaves.
4. Freely flowering habit.
5. Red purple-colored flowers.
6. Good garden performance.

In side-by-side comparisons conducted in Grand Haven, Mich., plants of the new *Weigela* differ primarily from plants of the female parent, 'Verweig', in the following characteristics:

1. Leaves of plants of the new *Weigela* are glossier than leaves of plants of 'Verweig'.
2. Plants of the new *Weigela* and 'Verweig' differ in leaf color as plants of 'Verweig' have green, white and red purple variegated leaves.

Plants of the new *Weigela* can be compared to plants of the *Weigela florida* 'Elvera', disclosed in U.S. Plant Pat. No. 12,217. In side-by-side comparisons plants of the new *Weigela* differed primarily from plants of 'Elvera' in the following characteristics:

1. Leaves of plants of the new *Weigela* were glossier than leaves of plants of 'Elvera'.
2. Plants of the new *Weigela* had darker-colored leaves than plants of 'Elvera'.
3. Plants of the new *Weigela* were more freely flowering than plants of 'Elvera'.
4. Plants of the new *Weigela* were more cold hardy than plants of 'Elvera'.

BRIEF DESCRIPTION OF THE PHOTOGRAPHS

The accompanying colored photographs illustrate the overall appearance of the new *Weigela* plant showing the colors as true as it is reasonably possible to obtain in colored reproductions of this type. Colors in the photographs may differ slightly from the color values cited in the detailed botanical description which accurately describe the colors of the new *Weigela* plant.

The photograph on the first sheet is a close-up view of a typical plant of 'SMNWFMS'.

The photograph on the second sheet is a close-up view of a typical flowering plant of 'SMNWFMS'.

DETAILED BOTANICAL DESCRIPTION

Plants used for the aforementioned photographs and the following description were grown during the summer in three-gallon containers in a polypropylene-covered shadehouse in Grand Haven, Mich. and under cultural practices typical of commercial *Weigela* production. During the production of the plants, day temperatures ranged from 18° C. to 27° C. and night temperatures ranged from 5° C. to 10° C. Plants of the new *Weigela* were two years old when the photographs and description were taken. Plants were overwintered in a polyethylene-covered greenhouse. In the following description, color references are made to The Royal Horticultural Society Colour Chart, 1995 Edition, except where general terms of ordinary dictionary significance are used.

Botanical classification: *Weigela florida* 'SMNWFMS'.

Parentage:

*Female or seed, parent.*—*Weigela florida* 'Verweig', disclosed in U.S. Plant Pat. No. 16,824.

*Male or pollen, parent.*—Unknown selection of *Weigela florida*, not patented.

Propagation:

*Type.*—By softwood cuttings.

*Time to initiate roots, summer.*—About 15 days at temperatures about 27° C.

*Time to produce a rooted young plant, summer.*—About two months at temperatures about 27° C.

*Root description.*—Fine; fibrous.

*Rooting habit.*—Freely branching; dense.

Plant description:

*Plant and growth habit.*—Perennial shrub; compact and low-mounding plant habit; rapid growth rate; vigorous growth habit.

*Branching habit.*—Freely branching habit with about 15 lateral branches developing per plant; pinching enhances lateral branch development; dense and bushy plant form.

*Plant height.*—About 45 cm.

*Plant diameter.*—About 70 cm.

Lateral branch description:

*Length.*—About 45 cm.

*Diameter.*—About 5 mm.

*Internode length.*—About 3 cm to 4.5 cm.

*Texture.*—Smooth, glabrous; woody with development.

*Strength.*—Strong.

*Aspect.*—About 40° to 45° from vertical.

*Color, developing.*—Close to 200B.

*Color, fully developed.*—Close to 197C.

Leaf description:

*Arrangement.*—Opposite; simple.

*Length.*—About 8 cm.

*Width.*—About 3.8 cm to 4 cm.

*Shape.*—Elliptic to oblanceolate.

*Apex.*—Acuminate to acute.

*Base.*—Cuneate to attenuate.

*Margin.*—Serrulate.

*Texture, upper and lower surfaces.*—Smooth, glabrous; leathery.

*Luster, upper surface.*—Glossy.

*Luster, lower surface.*—Slightly glossy.

*Venation pattern.*—Pinnate.

*Color.*—Developing leaves, upper surface: Close to 187A. Developing leaves, lower surface: Close to 200B. Fully expanded leaves, upper surface: Close to 202A; venation, close to 160A. Fully expanded leaves, lower surface: Close to 200B; venation, close to 160C.

*Petiole.*—Length: About 5 mm. Diameter: About 2 mm to 4 mm. Texture, upper and lower surfaces: Smooth, glabrous; towards the base, pubescent. Color, upper surface: Close to 160A. Color, lower surface: Close to 160C.

Flower description:

*Flower arrangement and habit.*—Salverform flowers arranged in terminal clusters of four to six flower each; flowers face mostly upright to slightly outwardly.

*Fragrance.*—None detected.

*Natural flowering season.*—Plants of the new *Weigela* flower from early to late spring in Grand Haven, Mich.; flowers not persistent.

*Flower cluster diameter.*—About 4 cm.

*Flower cluster height.*—About 6.5 cm.

*Flower diameter.*—About 1 cm.

*Flower length (height).*—About 3.3 cm.

*Flower throat diameter.*—About 3 mm.

*Flower tube length.*—About 1.5 cm.

*Flower tube diameter.*—About 3 mm.

*Flower buds.*—Length: About 3.4 cm. Diameter: About 1 cm. Shape: Obovate to spatulate. Color: Close to 61B.

*Corolla.*—Arrangement: Salverform; four petals fused into a tube with separate petal lobes. Petal lobe length: About 1.2 cm. Petal lobe width: About 9 mm. Petal lobe shape: Roughly orbicular. Petal lobe apex: Obtuse. Petal lobe margin: Entire; slightly undulate. Petal texture, upper and lower surfaces: Smooth, glabrous. Color: When opening, upper and lower surfaces: Close to 61C. Fully opened, upper and lower surfaces: Close to 61C; color does not fade with development.

*Sepals.*—Quantity per flower: Five in a single whorl, fused; campanulate calyx. Length: About 1 cm. Width: About 3 mm. Shape: Narrowly triangular, elongated. Apex: Acuminate. Margin: Entire. Sepal texture, upper and lower surfaces: Smooth; glabrous. Color, upper and lower surfaces: Close to 187B.

*Peduncles.*—Length: About 1.5 cm. Diameter: About 2 mm. Strength: Strong; flexible. Texture: Slightly pubescent. Color: Close to 187A.

*Reproductive organs.*—Stamens: Quantity and arrangement: Five per flower. Filament length: About 1.6 cm. Anther shape: Narrowly oblong. Anther size: About 8 mm. Anther color: Close to 155D. Pollen amount: None observed. Pistils: Quantity: One per flower. Pistil length: About 2.5 cm. Style length: About 2 cm. Style color: Close to 155A and 58A. Stigma color: Close to 160D. Ovary color: Close to 144D. Seeds and fruits: Seed and fruit development has not been observed on plants of the new *Weigela*.

Garden performance: Plants of the new *Weigela* have exhibited good tolerance to rain, wind and have been observed to tolerate temperatures from about −31° C. to about 38° C.

Pathogen & pest resistance: Plants of the new *Weigela* have been observed to be resistant to Mildew. Plants of the new *Weigela* have not been observed to be resistant to pests and other pathogens common to *Weigela* plants.

It is claimed:

1. A new and distinct *Weigela* plant named 'SMNWFMS' as illustrated and described.

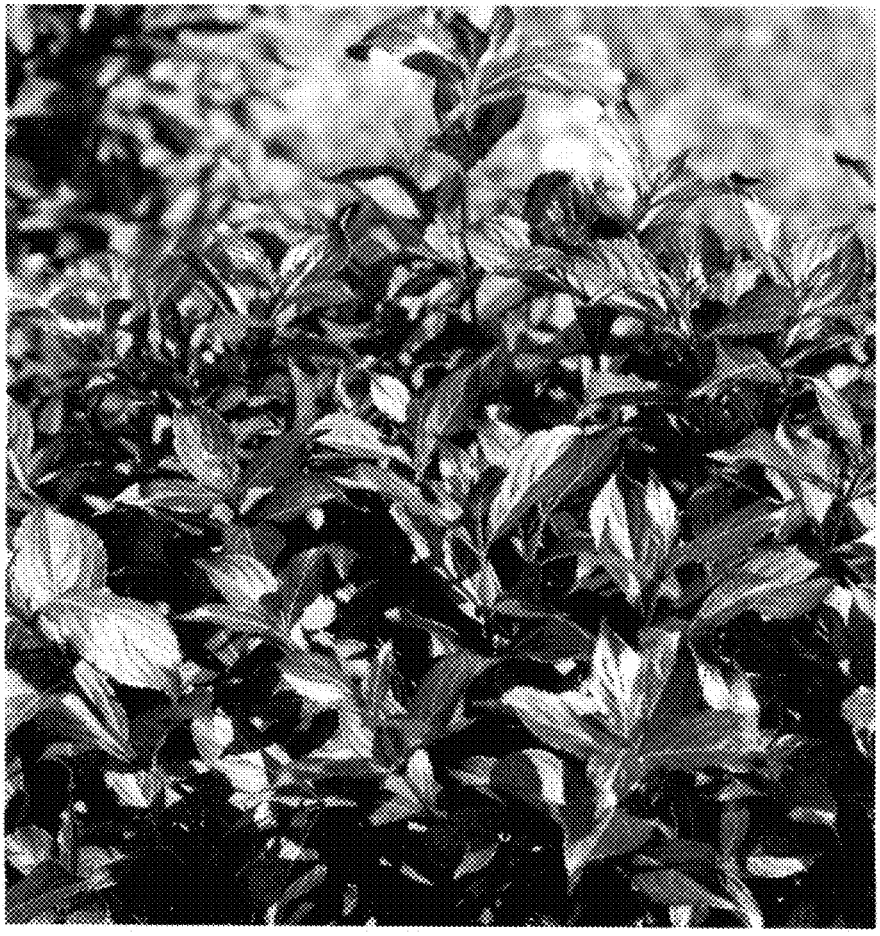

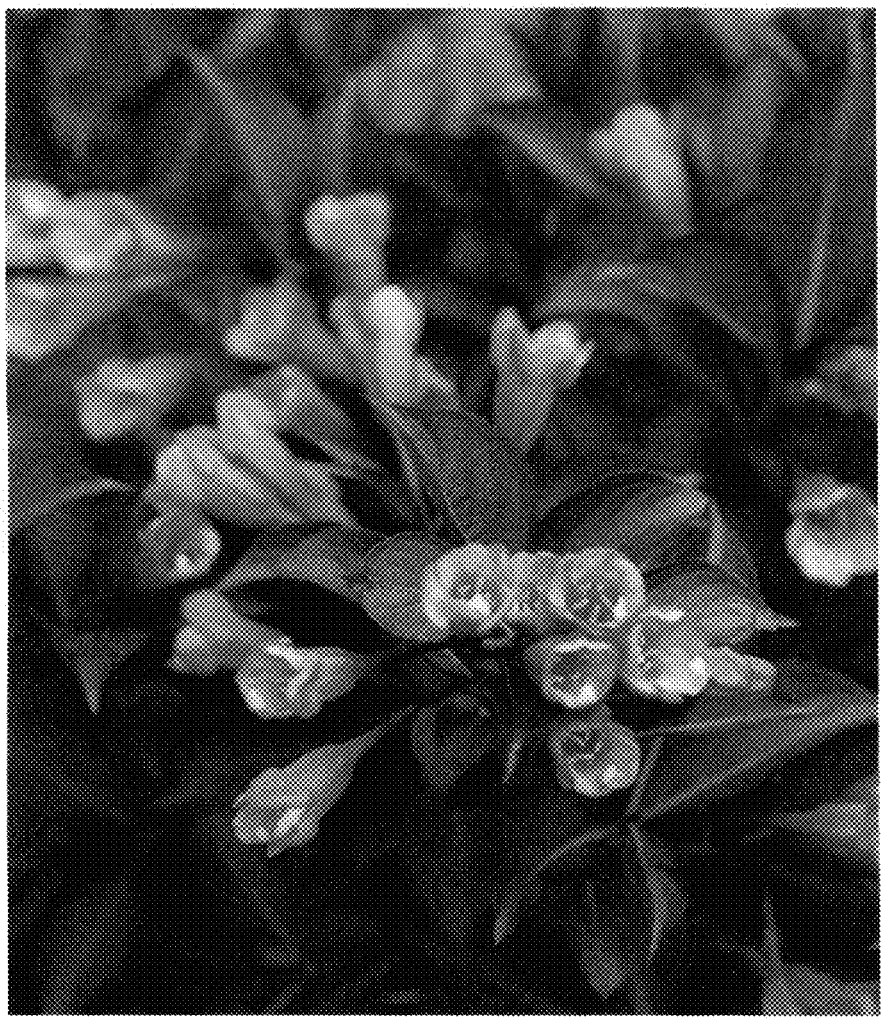

* * * * *